(12) United States Patent
Hu et al.

(10) Patent No.: US 11,724,024 B2
(45) Date of Patent: Aug. 15, 2023

(54) INVERTED BATTERY DEVICES, AND SYSTEMS AND METHODS FOR USE THEREOF

(71) Applicant: UNIVERSITY OF MARYLAND, COLLEGE PARK, College Park, MD (US)

(72) Inventors: Liangbing Hu, Potomac, MD (US); Chengwei Wang, College Park, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 828 days.

(21) Appl. No.: 16/520,120

(22) Filed: Jul. 23, 2019

(65) Prior Publication Data
US 2020/0030525 A1 Jan. 30, 2020

Related U.S. Application Data

(60) Provisional application No. 62/702,792, filed on Jul. 24, 2018.

(51) Int. Cl.
 *A61M 5/142* (2006.01)

(52) U.S. Cl.
 CPC . *A61M 5/14212* (2013.01); *A61M 2205/8206* (2013.01)

(58) Field of Classification Search
 None
 See application file for complete search history.

(56) References Cited

U.S. PATENT DOCUMENTS

| | | | | | |
|---|---|---|---|---|---|
| 4,731,049 | A | * | 3/1988 | Parsi | A61N 1/0448 604/20 |
| 5,322,502 | A | * | 6/1994 | Theeuwes | A61N 1/0444 604/20 |
| 2009/0005824 | A1 | * | 1/2009 | Visco | A61N 1/0448 607/3 |
| 2010/0312168 | A1 | * | 12/2010 | Yoshida | A61N 1/0436 604/20 |

OTHER PUBLICATIONS

Keplinger et al., "Stretchable, transparent, ionic conductors," *Science*, Aug. 2013, 341: pp. 984-987.

(Continued)

*Primary Examiner* — Manuel A Mendez
(74) *Attorney, Agent, or Firm* — RowanTree Law Group, PLLC; Frederick F. Rosenberger

(57) ABSTRACT

An inverted battery device has a pair of electrodes, first and second volumes, and an electrical conductor. One of the pair of electrodes is configured as an anode and the other is configured as a cathode. A first electrolyte solution and the anode are disposed in the first volume, while a second electrolyte solution and the cathode are disposed in the second volume. The electrical conductor extends between the first and second volumes to couple the pair of electrodes to each other such that electrons travel between the pair of electrodes. The device is constructed to produce ions rather than electrons such that an ionic current can be generated in a separate system, such as a biological system or other ionic system, when coupled between the anode and cathode.

20 Claims, 6 Drawing Sheets

(56) References Cited

OTHER PUBLICATIONS

Odgen et al., "Patch clamp techniques for single channel and whole-cell recording," *Microelectrode Techniques: The Plymouth Workshop Handbook* [online], 2nd Edition. Cambridge, UK: Company of Biologists, 1994 [retrieved on Jul. 22, 2019]. Retrieved from the Internet: <URL: http://www.utdallas.edu/~tres/microelectrode/microelectrodes_ch04.pdf>. Chapter 4, pp. 53-78, ISBN-10:0948601493.
Yang et al., "Ionic cable," *Extreme Mechanics Letters*, Mar. 2015, 3: pp. 59-65.
D'Andrea et al., "Propagation of intercellular $Ca^{2+}$ waves in mechanically stimulated articular chondrocytes," *FEBS Letters*, 1997, 400: pp. 58-64. (7 pages).
D'Hondt et al., "Thrombin Inhibits Intercellular Calcium Wave Propagation in Corneal Endothelial Cells by Modulation of Hemichannels and Gap Junctions," *Investigative Ophthalmology & Visual Science*, Jan. 2007, 48(1): pp. 120-133. (14 pages).
Fu et al., "All-Component Transient Lithium-Ion Batteries," *Advanced Energy Materials*, 2016, 6:1502496. (9 pages).
Galinski et al., "Ionic liquids as electrolytes," *Electrochimica Acta*, 2006, 51:5567-80. (14 pages).
Geddes et al., "Long-Term Lithium Therapy for Bipolar Disorder: Systematic Review and Meta-Analysis of Randomized Controlled Trials," *Am J Psychiatry*, Feb. 2004, 161(2): pp. 217-222. (6 pages).
Gierszewski et al., "Properties of $LiOH$ and $LiNO_3$ aqueous solutions: Additional results," *Fusion Engineering and Design*, 1992, 15: pp. 279-283. (5 pages).
Guo et al., "Integrating Ionic Gate and Rectifier Within One Solid-State Nanopore via Modification with Dual-Responsive Copolymer Brushes," *Advanced Functional Materials*, 2010, 20: pp. 3561-3567. (7 pages).
Hamill et al., "Improved Patch-Clamp Techniques for High-Resolution Current Recording from Cells and Cell-Free Membrane Patches," *Pflugers Archiv, European Journal of Physiology*, 1981, 391: pp. 85-100. (16 pages).
Kamaya et al., "A lithium superionic conductor," *Nature Materials*, Sep. 2011, 10: pp. 682-686. (5 pages).
Klepeis et al., "Growth factors but not gap junctions play a role in injury-induced $Ca^{2+}$ waves in epithelial cells," *Journal of Cell Science*, 2001, 114: pp. 4185-4195. (11 pages).
Knowles, Jeremy R., "Enzyme-catalyzed Phosphoryl Transfer Reactions," *Ann. Rev. Biochem.*, 1980, 49: pp. 877-919. (45 pages).
Li et al., "Leaf-Like $V_2O_5$ Nanosheets Fabricated by a Facile Green Approach as High Energy Cathode Material for Lithium-Ion Batteries," *Advanced Energy Materials*, 2013, 3: pp. 1171-1175. (5 pages).
Maj et al., "Long-Term Outcome of Lithium Prophylaxis in Bipolar Disorder: A 5-Year Prospective Study of 402 Patients at a Lithium Clinic," *Am J Psychiatry*, Jan. 1998, 155(1): pp. 30-35. (6 pages).
Niu et al., "$VO_2$ Nanowires Assembled into Hollow Microspheres for High-Rate and Long-Life Lithium Batteries," *Nano Letters*, 2014, 14: pp. 2873-2878. (6 pages).
Pan et al., "Template-Free Synthesis of $VO_2$ Hollow Microspheres with Various Interiors and Their Conversion into $V_2O_5$ for Lithium-Ion Batteries," *Angew. Chem. Int. Ed.*, 2013, 52: pp. 2226-2230. (5 pages).
Sakmann et al., "Patch Clamp Techniques for Studying Ionic Channels in Excitable Membranes," *Ann. Rev. Physiol.*, 1984, 46: pp. 455-472. (21 pages).
Sassi et al., "Increased gray matter volume in lithium-treated bipolar disorder patients," *Neuroscience Letters*, 2002, 329: pp. 243-245. (3 pages).
Sigworth et al., "Single Na+ channel currents observed in cultured rat muscle cells," *Nature*, Oct. 1980, 287: pp. 447-449. (3 pages).
Sproule, Beth, "Lithium in Bipolar Disorder: Can Drug Concentrations Predict Therapeutic Effect?," *Clin Pharmacokinet*, 2002, 41(9): pp. 639-660. (22 pages).
Table of contents for Kandel et al., *Principles of Neural Science*, 6th Edition, McGraw Hill Medical, New York, 2021. (4 pages).
Warren et al., "Mathematical modelling of calcium wave propagation in mammalian airway epithelium: evidence for regenerative ATP release," *Experimental Physiology*, 2009, 95.1: pp. 232-249. (18 pages).
Xu, Kang, "Nonaqueous Liquid Electrolytes for Lithium-Based Rechargeable Batteries," *Chem. Rev.*, 2004, 104: pp. 4303-4317. (116 pages).
Yameen et al., "Synthetic Proton-Gated Ion Channels via Single Solid-State Nanochannels Modified with Responsive Polymer Brushes," *Nano Letters*, 2009, 9(7): pp. 2788-2793. (6 pages).
Zhang et al., "Bioinspired Artificial Single Ion Pump," *Journal of the American Chemical Society*, 2013, 135: pp. 16102-16110. (9 pages).
Zhang et al., "Engineered Asymmetric Heterogeneous Membrane: A Concentration-Gradient-Driven Energy Harvesting Device," *Journal of the American Chemical Society*, 2015, 137: pp. 14765-14772. (8 pages).

* cited by examiner

INVERTED BATTERY DEVICES, AND SYSTEMS AND METHODS FOR USE THEREOF

CROSS-REFERENCE TO RELATED APPLICATIONS

The present application claims the benefit of U.S. Provisional Application No. 62/702,792, filed Jul. 24, 2018, which is hereby incorporated by reference herein in its entirety.

FIELD

The present disclosure relates generally to batteries, and more particularly, to inverted batteries that produce an external current based on ions instead of electrons.

BACKGROUND

Ion transport is a fundamental biological process in living systems, including humans, animals, plants, and microbes. The ions can act as charge carriers in various biological processes, such as conduction of nervous system signals. Moreover, adenosine triphosphate (ATP) molecules, which act to store and transport chemical energy within biological cells, normally exist as complex ions, and many biological activities in animals involve the transport of ions through ion channels of the cell membrane of living cells. For example, when a signal is transmitted along the axon of a neuron, $Na^+$ ions move into the neuron cell, and $K^+$ ions diffuse out of the cell through voltage-gated channels on the membrane. The potential of the cell membrane thus flips from negative to positive. After the signal passes, a sodium-potassium pump moves $Na^+$ ions out of and $K^+$ ions into the cell in order to reset the membrane potential to negative. Similar ionic processes based on the inflow or outflow of $Ca^{2+}$ (and/or other ions) occur in muscle cells to effect movement.

Since the dominating charge species in biosystems are ions, if a continuous ionic current can be supplied, ionic processes in the biosystem could be measured, and/or energy could be supplied to the biosystem. However, since electrons and ions travel in different media, electrical systems, such as conventional batteries, cannot directly interact with ionic systems. Rather, conventional batteries first cause an electrochemical reaction within the ionic system that generates such an ionic current. For example, conventional battery 12 (e.g., Li-ion battery) has a pair of electrodes connected by ionic medium 22 (e.g., liquid electrolyte) within battery housing 14, as shown in FIG. 1. One of the electrodes serves as a cathode 16 while the other electrode serves as an anode 18. Electrons 28 leave anode 18 and travel through an external circuit constituted by system 10 and electrical conductors 24, 26 to reach cathode 16. Simultaneously, ions 32 travel via ionic medium 22 internal to battery 12 from anode 18 through separator 20 to meet with electrons at cathode 16. Electrical current 30 thus flows through system 10 in a direction from cathode 16 to anode 18.

However, when system 10 comprises an ionic system such as a biological system, operation is different than in a typical electrical system. In particular, the charge carriers in an electrical system employing battery 12 are electrons 28 and holes, which cannot be transported by an ionic system. Rather, when the positive 16 and negative 18 electrodes of conventional battery 14 connect with ionic system 10 through electrical cables 24, 26, there will be no current without the occurrence of electrochemical reactions. Each electrochemical reaction has a threshold voltage (VE). As long as the applied voltage is less than this threshold voltage 306, the resulting current will be at or close to zero, as shown by curve 304 in FIG. 3. When the applied voltage reaches or exceeds the threshold voltage 306, a redox species will be reduced at the negative electrode 18 and be oxidized at the positive electrode 16. During these electrochemical reactions, electrons exchange at the corresponding electrode-electrolyte interfaces within the ionic system 10 and cause the current to increase, as shown by curve 304 in FIG. 3. But these electrochemical reactions can render the ionic system 10 unstable and may be fatal, or at least problematical, for living systems if such electrochemical reactions result in decomposition of cells, tissue, and/or water. Moreover, since most ionic processes in biosystems involve both low currents and low voltages, the electrical power offered by conventional batteries, which require application of a higher threshold voltage, cannot act as a suitable power source for biological systems.

Embodiments of the disclosed subject matter may address the above-mentioned problems and limitations, among other things.

SUMMARY

Embodiments of the disclosed subject matter provide an inverted battery device configured such that ions travel external to the battery rather than through an internal medium, so as to interface with an ionic system without corresponding electron-exchange electrochemical reactions in the ionic system. The inverted battery can have electrons travel internal thereto, for example, via appropriate electrical conductor(s) coupling the electrodes of the battery, rather than being directed through an external circuit. In some embodiments, the electrons can be directed through a separate external circuit, for example, to provide electrical power thereto and/or to allow control of the inverted battery. The externally-supplied ions can be used to generate an ionic current in the ionic system, such as a biological system. In certain non-limiting examples, the inverted battery can be used to provide selective pumping of ions, to deliver ions or ionized molecules (e.g., drug ions or molecules), to stimulate muscles or nerves in a biological system, and/or to remove ions from an ionic system.

In one or more embodiments, an inverted battery device comprises a pair of electrodes, first and second volumes, and an electrical conductor. One of the pair of electrodes is configured as an anode and the other of the pair is configured as a cathode. A first electrolyte solution and the anode are disposed in the first volume. A second electrolyte solution and the cathode are disposed in the second volume. The electrical conductor extends between the first and second volumes to couple the pair of electrodes to each other such that electrons travel between the pair of electrodes. The device is constructed to generate an ionic current in a separate system (e.g., ionic system) coupled between the anode and cathode. The ionic current can be generated without a corresponding electron-exchange electrochemical reaction in the ionic system.

In one or more embodiments, a system comprises an ionic system and an inverted battery coupled to the ionic system. The inverted battery is configured to supply ions to generate an ionic current in the ionic system. The ionic current can be generated without a corresponding electron-exchange electrochemical reaction in the ionic system.

In one or more embodiments, a method comprises using ions from an inverted battery to supply ions to an ionic system so as to generate an ionic current in the ionic system without a corresponding electron-exchange electrochemical reaction in the ionic system.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some elements may be simplified or otherwise not illustrated in order to assist in the illustration and description of underlying features. Throughout the figures, like reference numerals denote like elements.

DETAILED DESCRIPTION

Embodiments of the disclosed subject matter relate to inverted battery devices, and systems and methods for use thereof. As used herein, "inverted battery" refers to a design of an electrochemical energy storage device where the output charge carriers are ions instead of (or in addition) electrons. In contrast, conventional batteries (e.g., Li-ion batteries) only provide electrons as the output charge carriers, while ions are restricted to transport internal to the battery. As such, the term "electron battery" has also been used herein for the disclosed battery device in order to distinguish from conventional ion batteries. As used herein, the term "electron battery" is thus considered synonymous with "inverted battery." Note that "battery" as used herein can refer to a single cell or a collection of cells or cell assemblies, for example, in series or parallel configurations.

By providing ions as the output charge carriers, embodiments of the disclosed inverted batteries allow for generation of an ionic current within an ionic system without a corresponding electron-exchange electrochemical reaction in the ionic system. As used herein, "ionic system" refers to an aqueous medium having ions therein and that does not support the direct travel of electrons therein. Exemplary ionic systems include, but are not limited to, salt solutions and biological systems, such as living animal, plant, or microbial cells.

Embodiments of the inverted battery can be used for measurement or actuation of biological phenomena, selective pumping of ions, delivery of drug ions or ionized drug molecules, stimulation of muscle or nerve cells in a biological system, removal of ions from an ionic system, or for any other application that involves movement of ions. For example, since the dominating charge species in biosystems are ions, by supplying a continuous ionic current via the inverted battery, the ionic processes in the biosystem can be directly measured. Alternatively or additionally, energy could be supplied to the biosystem by the inverted battery. Other non-limiting examples for applications of the inverted battery are discussed in further detail elsewhere herein.

Embodiments of the inverted battery can include components similar to conventional ion batteries but reconfigured to allow for external ion transport. For example, FIG. 2 illustrates an exemplary configuration of an inverted battery 100. Similar to the conventional ion battery 12 of FIG. 1, inverted battery 100 includes a pair of electrodes, with one of the electrodes serving as a cathode 16 and the other serving as an anode 18. The cathode 16 and anode 18 can be formed of metal materials similar to those found in the electrodes of conventional ion batteries, such as, but not limited to, $Li^+$, $Na^+$, $K^+$, $Ca^{2+}$, $Mg^{2+}$ battery materials.

Figure 4A:
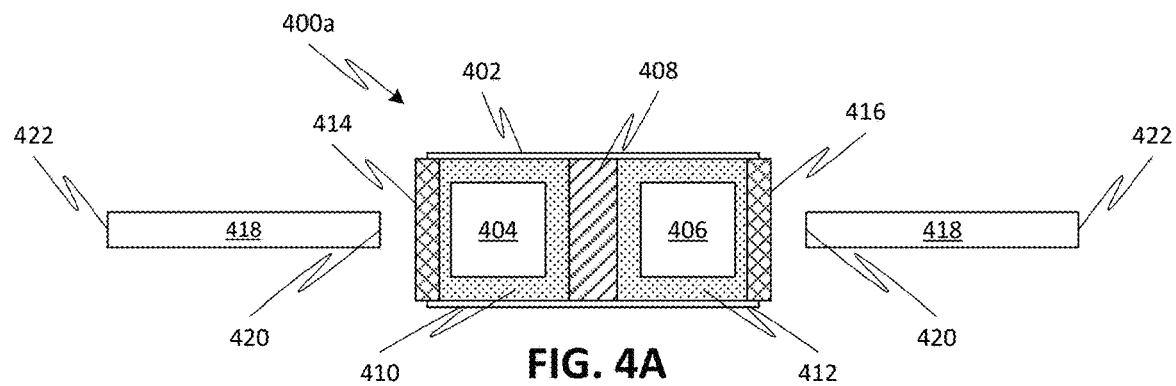
FIG. 4A is a simplified schematic diagram of an exemplary configuration of an inverted battery cell, according to one or more embodiments of the disclosed subject matter.
Figure 4B:
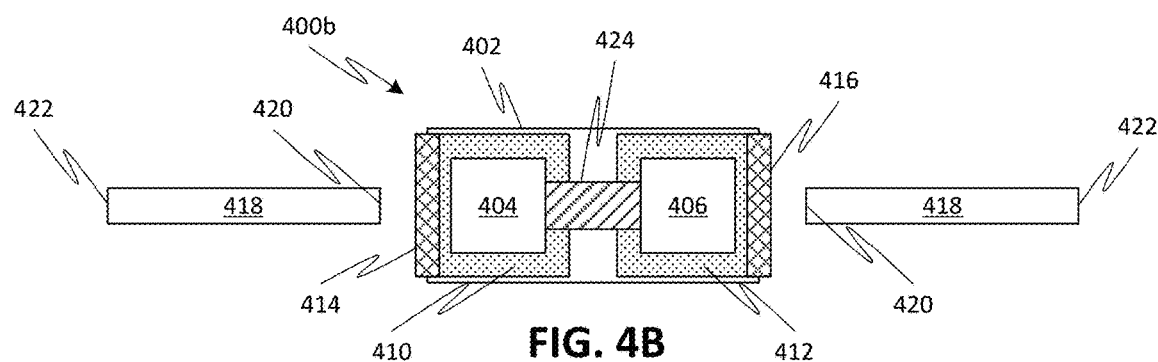
FIG. 4B is a simplified schematic diagram of another exemplary configuration of an inverted battery cell, according to one or more embodiments of the disclosed subject matter.
Figure 4C:
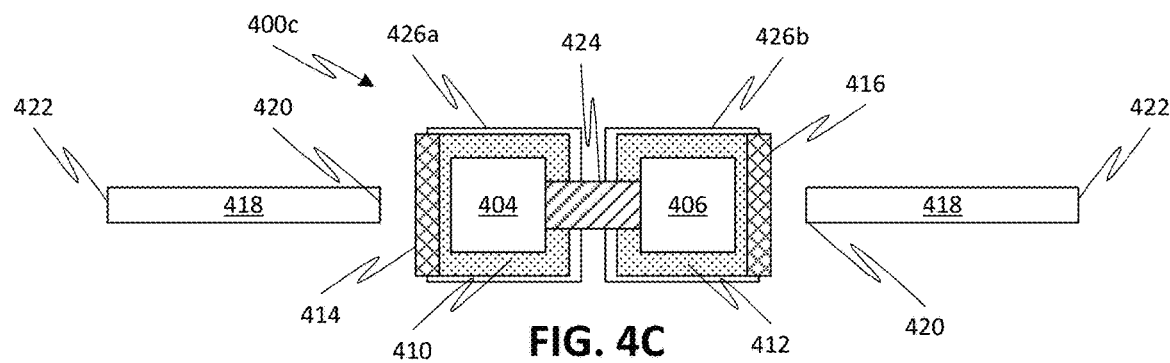
FIG. 4C is a simplified schematic diagram of yet another exemplary configuration of an inverted battery cell, according to one or more embodiments of the disclosed subject matter.

In contrast to ion battery 12, the cathode 16 and anode 18 of the inverted battery 100 are internally connected together by an electrical conductor such that electrons 108 are transported internal to housing 102 from the negative electrode 18 to the positive electrode 16 during discharge of the inverted battery. For example, housing 102 of the inverted battery 100 can be separated into a first volume 106a and a second volume 106b by an electrical conductor 104. The first volume 106a can be filled with a first electrical medium and contains the anode 18 therein. The second volume 106b can be filled with a second electrical medium and contains the cathode 16 therein. The first and second electrical medium may be different or the same, for example, an electrolyte solution. Electrons 108 from the anode 18 travel through the first electrical medium, across electrical conductor 104, and through the second electrical medium to reach the cathode 16. Alternatively, the cathode 16 and anode 18 may be directly connected to each other via the electrical conductor without intervening electrical media, for example, as illustrated in FIGS. 4B-4C and discussed in further detail below.

At the same time as travel of electrons 108 internal to the inverted battery, ions 110 travel from the anode 18 to the cathode 16 external to battery housing 102 during discharge of the inverted battery 100. For example, the electrodes 16, 18 of the inverted battery 100 can be connected to an ionic system 10 via respective ionic conductors 116, 114 to allow transport of ions between the inverted battery 100 and the ionic system 10. The ionic conductors can contain ions corresponding to the material of the electrodes 16, 18. For example, the ionic conductors can contain salts containing ions of the electrode materials or other ions and charged molecules. Additionally or alternatively, ionic conductors can contain ions different than the ions generated by electrodes 16, 18.

Figure 1:
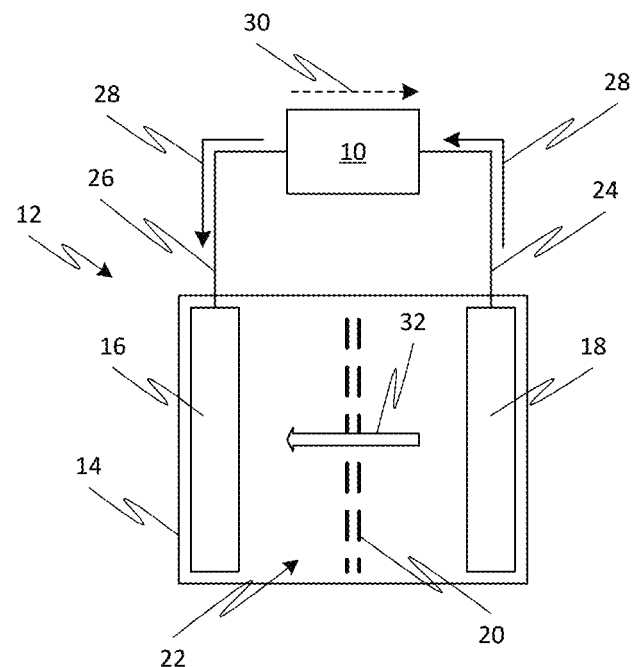
FIG. 1 is a simplified explanatory diagram of components of a conventional battery cell.
Figure 2:
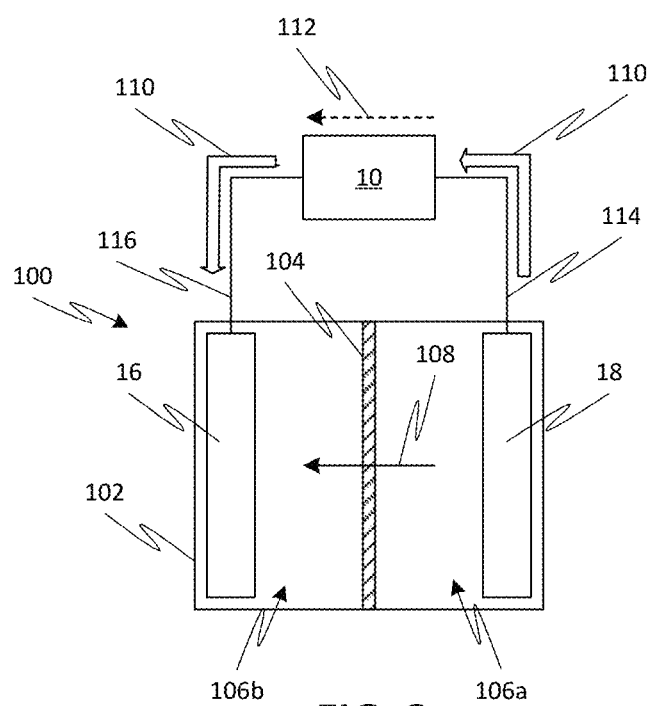
FIG. 2 is a simplified explanatory diagram of components of an inverted battery cell, according to one or more embodiments of the disclosed subject matter.

The inverted battery 100 can continuously generate ions to form an external ionic current 112 instead of forming an external electrical current 30 (as offered by the conventional battery of FIG. 1). By appropriate selection of materials for electrodes 16, 18 and corresponding ionic conductors 116, 114, the inverted battery 100 can be configured to generate ion flows of $Li^+$, $Na^+$, $K^+$, and/or $Ca^+$, which are typical ions in many biological processes. For example, the inverted battery 100 can be used to power the motion of ions in a biosystem.

Similar to conventional ion batteries, the inverted battery 100 can be constructed as either a primary battery (i.e., has a chemical composition that provides for only a single discharge cycle) or a secondary battery (i.e., is capable of being recharged to enable more than one discharge cycle). When the inverted battery 100 is constructed as a secondary battery, provision may be made to disconnect the battery 100 from the ionic system 10 prior to the recharging. In addition, individual inverted batteries 100 can be connected together in parallel (e.g., with cathodes 16 connected together and anodes 18 connected together by appropriate ionic conductors) or in series (e.g., with cathode 16 of one battery connected to the anode 18 of another battery) to achieve higher voltages and/or current for particular applications. Alternatively or additionally, individual battery cells 100 can be connected together in series by sharing an intervening ionic exchange membrane (e.g., where the ionic exchange membrane of the cathode volume of one battery is shared by the anode volume of an adjacent battery) or by directly coupling corresponding ionic exchange membranes (e.g., where the ionic exchange membrane of the cathode volume of one battery is in contact with the ionic exchange membrane of the anode volume of an adjacent battery).

Since the output charge carriers of the inverted battery 100 are ions, when its electrodes 16, 18 are coupled with an ionic system 10 through appropriate ionic conductors or cables 116, 114, the ions can enter or exit the ionic system 10 freely. Unlike the conventional battery 12, however, the ion interaction with the ionic system occurs without a threshold voltage for an electrochemical reaction. In particular, when the inverted battery 100 connects with an ionic system 10 through ionic conductors 114, 116, the charge-carrier ions will drift along the electrical field. Since both the ionic conductors 114, 116 and the ionic system are ionic mediums (i.e., capable of transporting ions), the charge-carrier ions can readily cross the electrode-electrolyte interface and travel in the ionic system without restriction.

Figure 3:
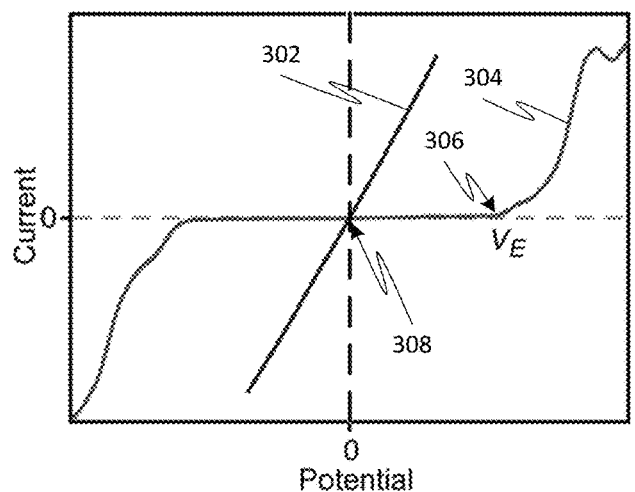
FIG. 3 is a graph of current-voltage curves for interaction of a conventional battery cell and the inverted battery cell with an ionic system.

As there is no electrochemical reaction controlling ion generation, there is no threshold voltage for operation of the inverted battery 100 with the ionic system 10. Thus, the ionic current 112 will follow Ohm's Law, where the current is linear with the applied voltage, as shown by curve 302 in FIG. 3. The slope of curve 302 is determined by the ionic resistance of the ionic system 10. This linearity can allow for fine control and tuning of the ionic current 112 by simply adjusting the applied voltage from zero (i.e., point 308) rather than requiring the elevated threshold voltage (i.e., point 306) of conventional batteries.

Thus, even with a small voltage bias by the inverted battery 100, a non-zero ionic current 112 can be achieved, which may be important when interfacing with biological systems where living cells or tissues may be delicate and voltage/currents involved may be relatively low. Since the inverted battery does not require a threshold voltage for operation with the ionic system, the inverted battery can interact with cells in the ionic system at any current/voltage level. Moreover, since no electrochemical reactions occur in the ionic system during the interaction, the inverted battery 112 can directly apply energy to the ionic system 10 (e.g., biological system) without otherwise causing decomposition of the electrolyte, cells, and/or tissues of the system 10. For example, in some embodiments, the tunable ionic current from the inverted battery could be used to change ion concentrations and/or charges outside of a cell membrane, resulting in the direct alteration of the membrane potential to modulate cellular behavior.

Although FIG. 2 illustrates a generalized configuration for the inverted battery 100, other configurations are also possible according to one or more contemplated embodiments. For example, FIG. 4A illustrates a first exemplary configuration for an inverted battery 400a, with ionic cables 418 for coupling the battery 400a to an ionic system. Battery 400a includes a first volume 410 and a second volume 412 separated from each other by an electrical conductor 408 within a common housing 402. A first electrolyte is disposed in the first volume 410 along with the cathode 404, while a second electrolyte is disposed in the second volume 412 along with the anode 406. As noted above, the electrolytes filling the respective first and second volumes may be of different or the same formulations, in particular, one that allows for ions and electrons to flow therethrough.

A first ion exchange membrane 414 is coupled to the first volume 410 and acts as an interface between the first volume 410 and the coupled ionic cable 418 to retain the first electrolyte within the first volume 410 while allowing ions to freely pass between the first electrolyte and the coupled ionic cable 418. Similarly, a second ion exchange membrane 416 is coupled to the second volume 412 and acts as an interface between the second volume 412 and the coupled ionic cable 418 to retain the second electrolyte within the second volume 412 while allowing ions to freely pass between the second electrolyte and the coupled ionic cable 418.

In some embodiments, the ionic cables 418 are separate components from the battery 400a (as shown in FIG. 4A) and are later coupled thereto, for example, at battery coupling end 420. Alternatively or additionally, the ionic cables 418 are formed as an integral party of the battery 400a, e.g., by direct connection to the appropriate ion exchange membrane of the battery 400a. An opposite interfacing end 422 of ionic cable 418 can be coupled to an ionic system for ionic communication. In some embodiments, interfacing end 422 of ionic cable 418 can includes its own ion exchange membrane to retain an electrolyte within the cable 418 while allowing ions to pass between the ionic system and the cable electrolyte. For example, the ionic cables 418 may have any of the configurations set forth in FIGS. 5A-5D or otherwise.

During discharge, ions generated in the second electrolyte by anode 406 travel from second volume 412 to coupling end 420 of ionic cable 418 via ion exchange membrane 416 and then on to the ionic system via interfacing end 422 of ionic cable 418. Similarly, ions travel from the ionic system via the other ionic cable 418 and onto cathode 404 by passing through ion exchange membrane 414 into the first electrolyte. Simultaneously, electrons generated in the second electrolyte by anode 406 travel from second volume 412 to the first electrolyte in first volume 410 via electrical conductor 408. When configured as a secondary battery by appropriate materials selection, the recharge process may occur in a reverse manner, i.e., where ions/electrons flow from cathode 404 to anode 406.

Note that since the electrical conductor 408 can only transport electrons, the conductor 408 acts as a barrier to ions in the separate volumes 410, 412. Thus, ions are physically prevented from internal transport between the first volume 410 and the second volume 412 by the conductor 408. Rather, ion transport is only possible by passing from the volumes 410, 412 through the respective ion exchange membranes 414, 416 to reach an external coupled ionic circuit via the ionic cables 418. Similarly, since the ion exchange membranes 414, 416 can only transport ions, the membranes 414, 416 act as barriers to retain the electrons within battery 400a. Thus, electrons are physically prevented by membranes 414, 416 from external transport between first volume 410 and second volume 412 via the coupled external ionic circuit.

Although electrical conductor 408 is shown contacting the electrolytes in the first and second volumes in FIG. 4A, other configurations for the electrical conductor are also possible according to one or more contemplated embodiments. For example, FIG. 4B illustrates another exemplary configuration of an inverted battery 400b where the anode and cathode are directly connected to each other by electrical conductor 424, e.g., a metal wire. The first volume 410 and the second volume 412 remain physically separated from each other by an intervening portion of housing 402. In effect, the electrical conductor 424 acts to short the cathode 404 and the anode 406 together with respect to electrons. However, since the electrical conductor 424 is incapable of transporting ions, ions must still pass through the external ionic circuit (i.e., via membranes 414, 416 and ionic cables 418) in order to travel between the cathode 404 and the anode 406.

Although the first volume 410 and second volume 412 are shown as contained in a common housing 402 in FIGS. 4A-4B, separated housing configurations are also possible according to one or more contemplated embodiments. For example, FIG. 4C illustrates another exemplary configuration of an inverted battery 400c where the first volume 410 is contained in a first housing 426a and the second volume 412 is contained in a second housing 426b separate from the first housing 426a. Electrical conductor 424 can thus extend externally between the two housings 426a, 426b to connect cathode 404 and anode 406 together, similar to FIG. 4B. Alternatively or additionally, electrical conductor 424 in FIG. 4C can couple the electrolyte in first volume 410 with the electrolyte in second volume 412 without directly contacting cathode 404 and anode 406, similar to the configuration illustrated in FIG. 4A. In either case, since electrical conductor 424 is incapable of transporting ions, ions must still pass through the external ionic circuit (i.e., via membranes 414, 416 and ionic cables 418) in order to travel between cathode 404 and anode 406.

In any of the disclosed embodiments, ionic conductors (e.g., ionic cables 418 in FIGS. 4A-4C) facilitate the transport of ions similar to how electrical conductors transport electrons, although available ionic conductors may offer conductivities that are much smaller (e.g., at least an order of magnitude) than their electrically conducting counterparts. Composition of the ionic conductor may be selected based on the desired ion to transport. For example, the ionic conductors can be formed of an ion-conducting polymer, an ion-conducting ceramic, an ionic liquid, a salt solution, cellulose (e.g., nanofibrous cellulose or bacterial cellulose), hydrogel, or composites or combinations thereof. The material of the ionic conductor may have the same ions produced by the battery or have ions different than those produced by the battery.

Figure 5A:
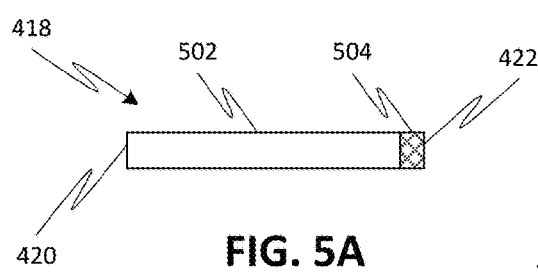
FIG. 5A is a simplified schematic diagram of an exemplary configuration of an ionic conductor for use with an inverted battery cell, according to one or more embodiments of the disclosed subject matter.

For example, FIG. 5A illustrates an exemplary configuration for ionic cable 418 (i.e., ionic conductor) for use with an inverted battery. In preparation for operation, battery coupling end 420 of the ionic cable 418 can be coupled to the battery, while opposite interfacing end 422 can be coupled to the ionic system. At interfacing end 422, the ionic cable 418 can include an ion exchange membrane 504 that isolates any ion-conducting material within body 502 of the ionic cable 418 from the ionic system while allowing ions to pass therebetween.

Figure 5B:
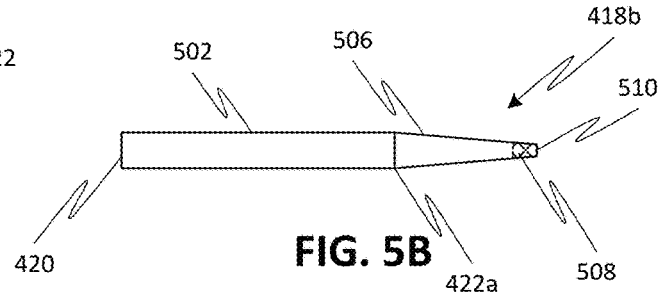
FIG. 5B is a simplified schematic diagram of another exemplary configuration of an ionic conductor for use with an inverted battery cell, according to one or more embodiments of the disclosed subject matter.

In some embodiments, the ionic cable may be provided with an extension at the end opposite the battery coupling end 420 to more easily interface with portions of the ionic system, for example, cells in a biological system. For example, FIG. 5B illustrates another exemplary configuration for an ionic cable 418b, where narrowing extension 506 has been coupled to body 502 at interfacing end 422a thereof. The narrowing extension 506 may have its own ion exchange membrane 508 at interfacing end 510 that isolates any ion-conducting material within narrowing extension 506 from the ionic system while allowing ions to pass therebetween. This membrane 508 may be in addition to or in place of ion exchange membrane 504 (not shown in FIG. 5B) at interfacing end 422a. For example, narrowing extension 506 may be a syringe-tip filled with a salt solution.

Although shown in FIG. 5B as narrowing (i.e., cross-section that decreases along its length) in order to interface with portions of the ionic system, other structural configurations and/or uses for extension 506 are also possible according to one or more contemplated embodiments. For example, the extension 506 may be non-narrowing (i.e., constant cross-section), variable, or expanding (i.e., cross-section that increases along its length). Alternatively or additionally, the extension 506 may have ions (i.e., second ions) different from those in the body 502 (i.e., first ions) of the ionic cable 502. Flow of the first ions from body 502 into the extension 506 may thus deliver the different second ions into the ionic system from the extension 506. In this manner, the type of ions delivered to the ionic system can be decoupled from the electrode materials and type of ions produced by the inverted battery and/or the type of ions in the ionic cable body 502. Other configurations are also possible, for example, where extension 506 is provided between the coupling end 420 and the corresponding ionic membrane of the inverted battery.

Figure 5C:
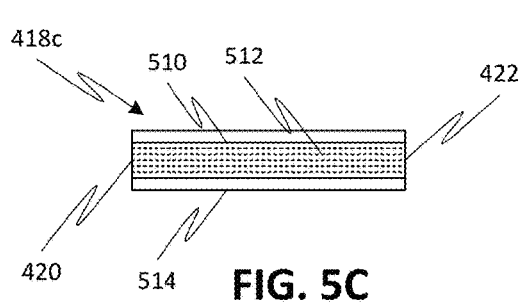
FIGS. 5C-5D are a simplified schematic diagram and 3-D cutaway view, respectively, of yet another exemplary configuration of an ionic conductor for use with an inverted battery cell, according to one or more embodiments of the disclosed subject matter.
Figure 5D:
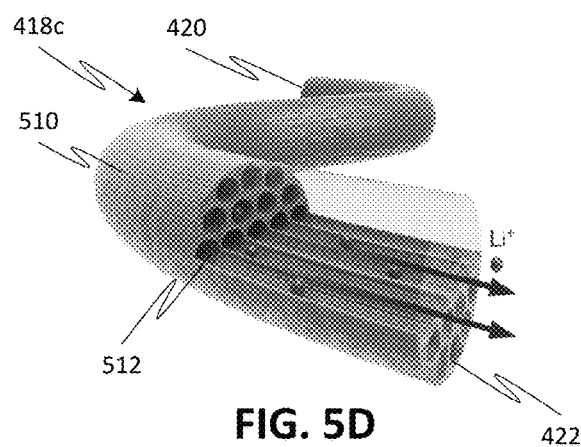

In some embodiments, an ionic cable can be comprised of base structure that supports an ion-conducting material therein. For example, the base structure may be a porous material and/or have a plurality of axially-extending lumen therein. The ion-conducting material, e.g., a salt solution, polymer, or hydrogel, can infiltrate the pores or lumen of the base structure to form a composite material capable of transporting ions therethrough. The base structure thus can provide mechanical strength to an ion-conducting material otherwise incapable of independently maintaining its shape. For example, FIGS. 5C-5D illustrate an ionic cable 418c where a natural grass stem 510 is used as the base structure. The grass stem 510 has numerous axially-extending lumen 512 (e.g., microchannels or micro-vessels) that are filled with an aqueous ion-conducting salt solution. A seal or covering 514 (e.g., shrink tubing) can be formed over an outer circumferential surface of the grass stem 510. For example, the covering 514 can help prevent, or at least reduce, evaporation of the aqueous salt solution contained within the lumen 512, and/or protect the grass stem 510 from damage due to handling.

Although the above noted example utilizes a grass stem as the base structure, other materials for the base structure are also possible according to one or more contemplated embodiments. For example, the base structure can comprise a single-channel or multi-channel capillary tube, a structure with one or more micro-channels or nano-channels, a micro-porous or nano-porous structure, or any other structure capable of containing the aqueous salt solution. Moreover, although the above noted examples utilize an aqueous salt solution as the ion-conducting material, other materials for the ion-conducting material are also possible according to one or more contemplated embodiments. For example, the base structure can be infiltrated with an ion-conducting polymer (e.g., using a fluid polymer precursor that polymerizes in situ) or hydrogel, which may also improve the structural reliability of the base structure.

Figure 6A:
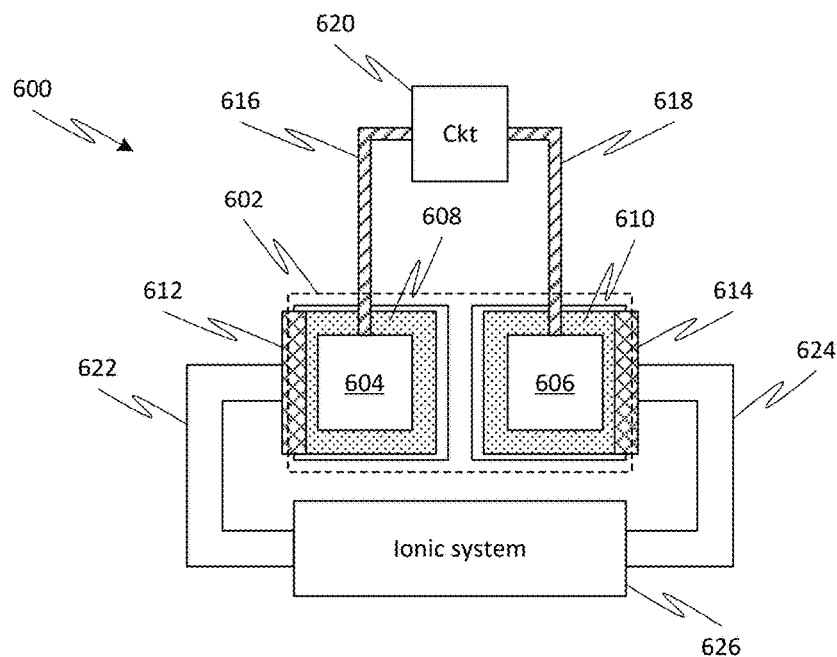
FIG. 6A is a simplified schematic diagram of an exemplary setup for an inverted battery cell to simultaneously interact with an ionic system and power an external electronic circuit, according to one or more embodiments of the disclosed subject matter.

Similar to conventional batteries, an external control system or operating circuit can be coupled to the inverted battery to control operation thereof, in particular, to control a level or on/off operation of the ionic current flow in the ionic system. For example, FIG. 6A illustrates a setup 600 for control of inverted battery 602 when coupled to ionic system 626. Similar to previously described configurations, inverted battery 602 includes a cathode 604 disposed in a first volume 608 with a first electrolyte and an anode 606 disposed in a second volume 610 with a second electrolyte. A first ion exchange membrane 612 couples the first volume 608 to a first ionic cable 622, and a second ion exchange membrane 614 couples the second volume 610 to a second ionic cable 624. The first and second ionic cables 622, 624 thus couple the inverted battery 602 to the ionic system 626 for ion transport therebetween.

Electrical connection for transfer of electrons between the cathode 604 and the anode 606 is made by electrical conductors 616, 618 and circuit 620, which may be considered part of the battery 602 (i.e., when housed in a common housing) or separate from the battery 602 (i.e., when the electrical conductors 616, 618 extend outside the battery housing to reach the external circuit 620). In some embodiments, the circuit 620 can control the flow of electrons therethrough, which in turn controls the flow of electrons between the cathode 604 and the anode 606. This control of electron flow directly influences the ion flow between the cathode 604 and the anode 606 in the external circuit (i.e., ionic cables 622, 624 and ionic system 626). Thus, circuit 620 provides a mechanism for control of the resulting ionic current via manipulation of the internal electron flow.

Alternatively or additionally, circuit 620 may not necessarily control operation of the battery 602. Rather, the electron flow between anode 606 and cathode 604 may simply be used to provide electrical power to circuit 620 in a manner similar to a conventional battery. For example, circuit 620 may be a sensing circuit (e.g., for sensing an external condition or for sensing a magnitude of ionic current based on electron flow between the anode 606 and cathode 604), an input/output circuit (e.g., for communicating with an external circuit, such as when setup 600 is part of a device implanted in a biological system), a logic circuit (e.g., for determining when/how to operate the inverted battery, for example to deliver a drug), or any other type of circuit that runs on electrical power.

Figure 6B:
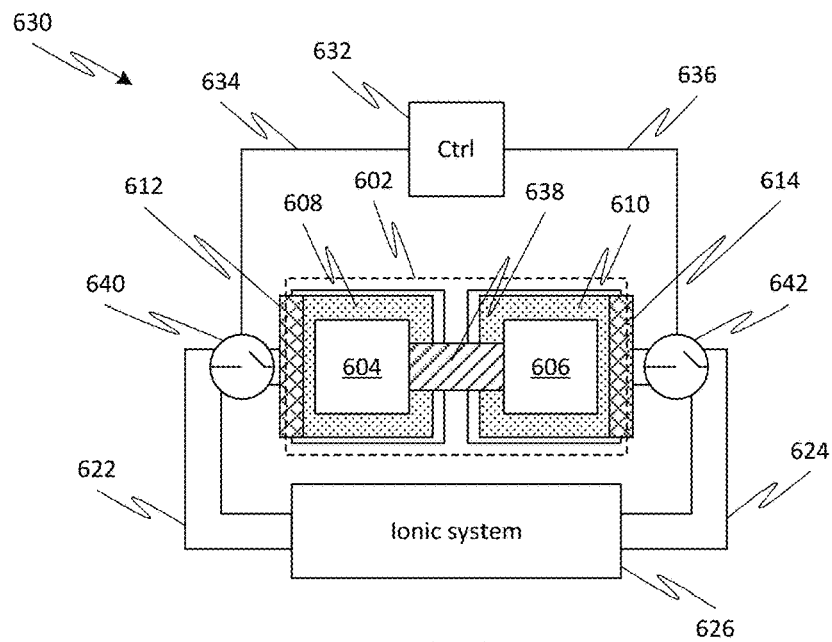
FIG. 6B is a simplified schematic diagram of an exemplary setup for controlling the interaction of an inverted battery cell with an ionic system, according to one or more embodiments of the disclosed subject matter.

FIG. 6B illustrates another exemplary setup 630 for control of inverted battery 602 when coupled to ionic system 626. In contrast to FIG. 6A, control of the ionic current is provided via external switching mechanisms rather internal control of electron flow. In particular, each ionic cables 622, 624 can be provided with an appropriate switching device 640, 642 that provides on/off control of ion flow therethrough, while the cathode 604 and anode 606 are electrically connected together by electrical conductor 638. For example, switching devices 640, 642 may be a physical switching mechanism that brings portions of the respective ionic cable into or out of contact with each other, thereby allowing or preventing ion flow depending on the configuration. Other types of switching mechanisms are also possible according to one or more contemplated embodiments. Although two switching devices 640, 642 are shown, it is also possible to employ a single switching device coupled to one of the ionic cables 622, 624.

A control module 632 (i.e., a control circuit or microprocessor) can be connected via signal connection lines 634, 636 to each switching device 640, 642 to control operation thereof. The control module 632 can receive electrical power from a separate power source (not shown). Alternatively or additionally, the control module 632 can be coupled to electrical conductor 638 to receive electrical power from the electron flow between the cathode 604 and the anode 606, similar to the configuration in FIG. 6A.

Figure 7:
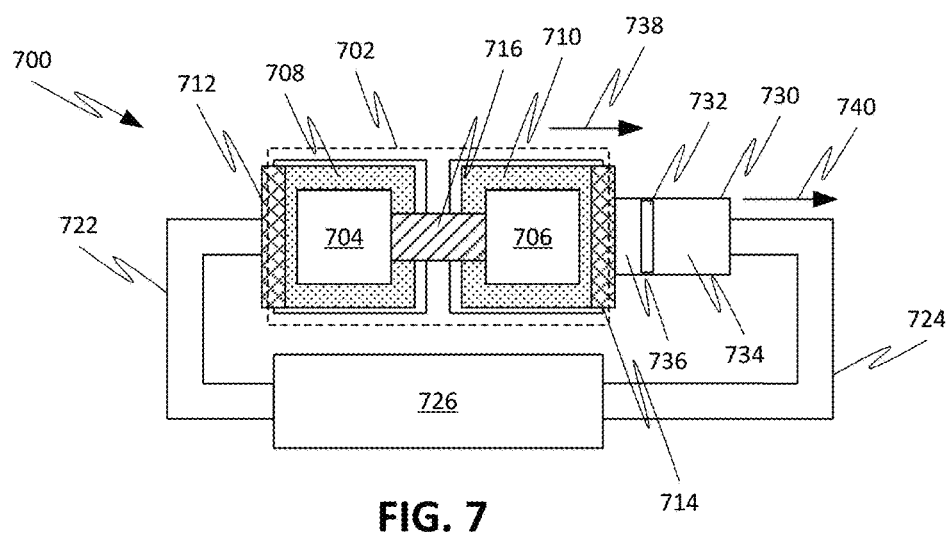
FIG. 7 is a simplified schematic diagram of an exemplary setup for drug delivery to an ionic system using an inverted battery cell, according to one or more embodiments of the disclosed subject matter.

In addition to measurement of biological systems, embodiments of the disclosed inverted battery can be used in any ionic system application where provision and/or transport of ions may be useful. For example, FIG. 7 illustrates an exemplary setup 700 for use of an inverted battery 702 for delivery of a drug 740 to a biological system 726. Similar to previously described configurations, inverted battery 702 includes a cathode 704 disposed in a first volume 708 with a first electrolyte and an anode 706 disposed in a second volume 710 with a second electrolyte. Cathode 704 and anode 706 are electrically connected together by electrical conductor 716 to allow electron transport therebetween. A first ion exchange membrane 712 couples the first volume 708 to a first ionic cable 722, and a second ion exchange membrane 714 is coupled to the second volume 710. A drug reservoir 730 can be coupled between the second ion exchange membrane 714 and a second ionic cable 724. The first and second ionic cables 722, 724 are coupled at respective interfacing ends to the biological system 726.

In discharging the inverted battery 702, positively charged ions 738 from the second volume 710 pass through the second ion exchange membrane 714 into an antechamber 736 of the drug reservoir 730. The antechamber 736 can be separated from a main chamber 734 of the drug reservoir 730 by another ion exchange membrane 732. The main chamber 734 can contain drug ions or charged drug molecules. Ion flow 738 from the inverted battery 702 into the antechamber 736 can cause a similar flow 740 of drug out of drug reservoir 730 into ionic cable 724 and eventually into biological system 726. Thus, the ionic current of the inverted battery 702 is effective to pump the charged drug and deliver it to targets within the biological system 726. Moreover, the provision of the drug reservoir 730 allows for decoupling from the electrode materials of the inverted battery 702, such that setup 700 can deliver a drug that is different than ions generated by the inverted battery 702.

When the drug to be delivered has a positive charge, the drug reservoir 730 can be provided on the anode side of the inverted battery 702, as illustrated in FIG. 7. Alternatively or additionally, when the drug to be delivered has a negative charge, the drug reservoir 730 can be provided on the cathode side of the inverted battery, e.g., between first ion exchange membrane 712 and first ionic cable 722.

In some embodiments, the drug may be ions, such as $Li^+$, $Na^+$, $K^+$, and/or $Ca^{2+}$. In such configurations, the provision of a separate drug reservoir 730 may be unnecessary as the inverted battery itself can directly generate the desired drug ion. For example, lithium ($Li^+$) has been used as an effective treatment for bipolar disorder. However, lithium can cause side-effects especially at high dosages. In embodiments, an implantable device including an inverted battery having a lithium anode (i.e., acting as a $Li^+$ source) can be used to deliver lithium to a patient on demand and in a targeted manner, thereby increasing treatment efficacy and reducing dosage risks and side effects. Alternatively or additionally, the drug can be a complex drug molecule functionalized with charges and contained within chamber 734 of the reservoir.

Figure 8:
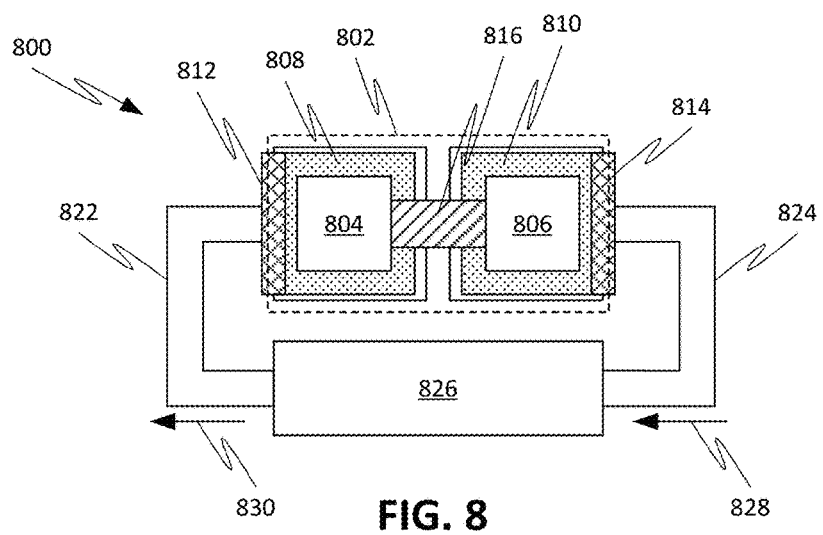
FIG. 8 is a simplified schematic diagram of an exemplary setup for biocompatible stimulation and/or pumping of ions from an ionic system using an inverted battery cell, according to one or more embodiments of the disclosed subject matter.

FIG. 8 illustrates another exemplary setup 800 for use of an inverted battery 802 for ion-based interaction with a biological system 826. Similar to previously described configurations, inverted battery 802 includes a cathode 804 disposed in a first volume 808 with a first electrolyte and an anode 806 disposed in a second volume 810 with a second electrolyte. Cathode 804 and anode 806 are electrically connected together by electrical conductor 816 to allow electron transport therebetween. A first ion exchange membrane 812 couples the first volume 808 to a first ionic cable 822, and a second ion exchange membrane 814 couples the second volume 810 to a second ionic cable 824. The first and second ionic cables 822, 824 are coupled at respective interfacing ends to the biological system 826.

In some embodiments, the ion-based interaction may deliver ions 828 to one or more cells of the biological system 826, e.g., muscle or nerve cells, to stimulate a response. The ionic current of the inverted battery 802 can thus be used as biocompatible stimuli to interact with muscle and nerve systems in humans or animals. Such ionic stimulation can be used for physical therapy, muscle stimulation, recovery of damaged muscles or nerves, and/or monitoring of biosystem health. Alternatively or additionally, the ion-based interaction of the inverted battery 802 can pump ions 830 from the biological system 826, which may be effective to treat certain conditions or diseases of the biological system 826.

In some embodiments, the inverted battery 802 may be an integral part of a machine-assistive device, where the machine-assistive device is used to control or interact with body movements of the human or animal. Such a machine-assistive device can be used for the treatment of paralysis or nerve system damage, treatment of heart disease (e.g., by altering heart contractions), treatment of Alzheimer's/Parkinson's disease (e.g., by controlling neuron stimulation), and/or treatment of any other disease that causes muscle or nerve damage.

Figure 9:
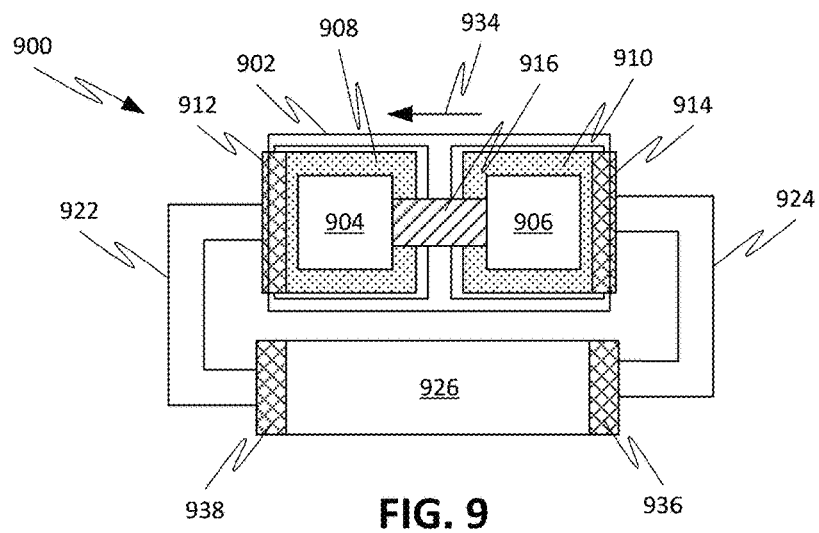
FIG. 9 is a simplified schematic diagram of an exemplary generalized setup for ion pumping using an inverted battery cell, according to one or more embodiments of the disclosed subject matter.

FIG. 9 illustrates another exemplary setup 900 for use of an inverted battery 902 for selective pumping of ions. Similar to previously described configurations, inverted battery 902 includes a cathode 904 disposed in a first volume 908 with a first electrolyte and an anode 906 disposed in a second volume 910 with a second electrolyte. Cathode 904 and anode 906 are electrically connected together by electrical conductor 916 to allow electron transport 934 therebetween. A first ion exchange membrane 912 couples the first volume 908 to a first ionic cable 922, and a second ion exchange membrane 914 couples the second volume 910 to a second ionic cable 924.

The first and second ionic cables 922, 924 are coupled at respective interfacing ends to an ionic system 926, for example, a salt solution. In particular, the interfacing ends of each of the ionic cables 922, 924 includes a respective ionic exchange membrane 938, 936. The type of ionic exchange membranes 936, 938 can be chosen to achieve selective pumping based on the generated ionic current. For example, the ionic exchange membranes 936, 938 can each be one of a cation exchange membrane (that allows positive ions to travel through but prevents negative ions from passing) and an anion exchange membrane (that allows negative ions to travel through but prevents positive ions from passing).

For example, the inverted battery 902 can generate $Y^+$ ions (e.g., $Li^+$) at the anode 906, each ionic cable 922, 924 includes a salt formed of $Y^+X^-$, and the ionic system includes a salt formed of $A^+B^-$, where A and B may the same or different from Y and X, respectively. By appropriate selection of the types for membranes 936, 938, changes in each of the conductors 922, 924 and ionic system 926 can be effected upon discharge of the inverted battery 902, as summarized in Table 1 below.

For example, when membrane 938 of the cationic-side cable 922 is selected to be a cation exchange membrane and membrane 936 of the anionic-side cable 924 is also selected to be cation exchange membrane, discharge of battery 902 causes the concentration of $A^+$ ions in the cationic-side cable 922 to increase while the concentration of $A^+$ ions in the ionic system 926 decreases, in effect pumping the $A^+$ ions out of the ionic system 926. In another example, when membrane 938 of the cationic-side cable 922 is selected to be an anion exchange membrane and membrane 936 of the anionic-side cable 924 is also selected to be an anion exchange membrane, discharge of battery 902 causes the concentration of $Y^+$ and $B^-$ ions in the anionic-side cable 924 to increase while the concentration for $B^-$ ions in the ionic system 926 decreases, in effect pumping the B⁻ ions out of the ionic system 926. In yet another example, when membrane 938 of the cationic-side cable 922 is selected to be an anion exchange membrane and membrane 936 of the anionic-side cable 924 is selected to be a cation exchange membrane, discharge of battery 902 causes the concentration of $Y^+$ and $X^-$ to increase in the ionic system 926, in effect pumping ions from the cable 922 into the ionic system.

TABLE 1

Change in concentration of ions in the ionic conductors and in the ionic system based on selection of the type of ion exchange membranes of the ionic conductors.

| Membrane 936 | Membrane 938 Ion | Cation Exchange Membrane | | | Anion Exchange Membrane | | |
|---|---|---|---|---|---|---|---|
| | | Conductor 922 | Conductor 924 | Ionic system 926 | Conductor 922 | Conductor 924 | Ionic system 926 |
| Cation Exchange Membrane | $Y^+$ | Decrease | No Change | Increase | Decrease | No Change | Increase |
| | $X^-$ | No Change | No Change | None | Decrease | No Change | Increase |
| | $A^+$ | Increase | None | Decrease | None | None | No Change |
| | $B^-$ | None | None | None | None | None | No Change |
| Anion Exchange Membrane | $Y^+$ | Decrease | Increase | None | Decrease | Increase | None |
| | $X^-$ | No Change | No Change | None | Decrease | No Change | Increase |
| | $A^+$ | Increase | None | Decrease | None | None | No Change |
| | $B^-$ | None | Increase | Decrease | None | Increase | Decrease |

In still another example, when membrane 938 of the cationic-side cable 922 is selected to be a cation exchange membrane and membrane 936 of the anionic-side cable 924 is selected to be an anion exchange membrane, discharge of battery 902 causes the concentration of $A^+$ and $B^-$ to decrease in the ionic system 926, in effect pumping ions out of the ionic system. Such a configuration can be used for desalination, whereby the salt NaCl is removed from salt water (as the ionic system) by simply selecting an anion exchange membrane for anionic-side ionic cable and a cation exchange membrane for the cationic-side ionic cable and applying ionic current via the inverted battery. Of course, other applications for the ion-pumping configurations of Table 1 are also possible according to one or more contemplated embodiments.

Example 1

Figure 10A:
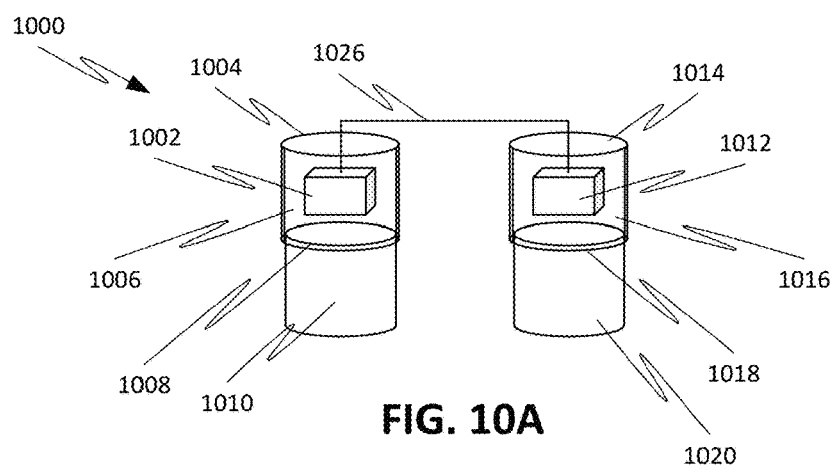
FIG. 10A illustrates the configuration of a fabricated example of an inverted battery cell, according to one or more embodiments of the disclosed subject matter, used for characterization and testing.
Figure 10B:
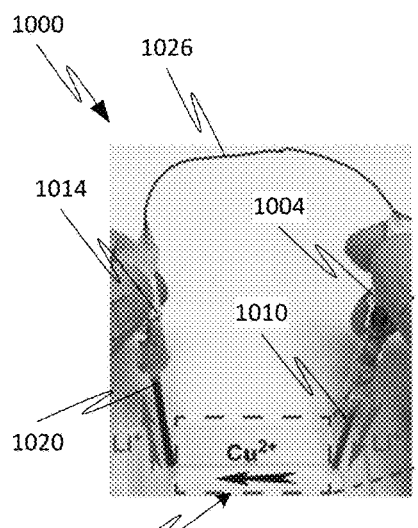
FIG. 10B is a photo of the inverted battery cell of FIG. 10A in operation to drive $Cu^{2+}$ ions in an ionic system.

An inverted battery 1000 was fabricated according to the configuration illustrated in FIG. 10A. In particular, the anode 1002 was formed of a lithium metal and the cathode 1012 was formed of vanadium oxide ($V_2O_5$). Both the anode 1002 and the cathode 1012 were sealed in respective glass tubes 1004, 1014 filled with organic electrolyte 1006, 1016, in particular, 1M $LiPF_6$ in ethylene carbonate/diethyl carbonate (1:1 vol %) electrolyte. One end of each glass tube 1004, 1014 was sealed with a respective ion exchange membrane 1008, 1018, in particular, a cation exchange membrane, that retained the electrolyte 1006, 1016 while allowing ions ($Li^+$) to pass through. The electrodes 1002, 1012 were coupled together by an electrically conductive wire 1026, which allowed transport of electrons and served as the internal circuit of the inverted battery 1000.

To achieve further enhancements in performance, the cathode 1012 was formed of $V_2O_5$ nanowires synthesized by a hydrothermal method. The diameters of the $V_2O_5$ nanowires were around several tens of nanometers, while their lengths were several micrometers. This high aspect ratio allowed the nanowires to form a network structure, which decreased the distance of lithium ion diffusion and facilitated the transportation of electrons. These $V_2O_5$ nanowires were synthesized by adding 0.8 g of $V_2O_5$ powder to 60 mL of de-ionized water and stirring for 1 h. Subsequently, 10 mL of 30% hydrogen peroxide was added to the solution and continuously stirred for 2 h. The resulting solution was heated at 210° C. for 100 h in an autoclave to facilitate the hydrothermal reaction. The final $V_2O_5$ nanowires were washed with de-ionized water several times and vacuum filtrated into a film. The $V_2O_5$ nanowire film was cut into small pieces and wrapped in a conductive carbon cloth to serve as the cathode 1012.

For ionic cables 1010, 1020 coupled to the ion exchange membranes 1008, 1018 to serve as parts of the external circuit, a natural grass stem soaked in an aqueous salt solution was used. The grass stem was from the *Poa pratensis* species, a common lawn grass. Each grass stem has a length of 30-50 cm and a relatively uniform diameter of 1-2 mm. The stem of natural grass is full of micro-vessels, which are vertically aligned across the entire blade of grass. The size of the micro-vessels varied from several micrometers to several tens of micrometers, which was suitable for absorbing and containing the electrolyte solution due to capillary effects.

When these longitudinally continuous vessels of the natural grass (after removal of leaves) were filled with the aqueous salt solution, they acted as an ionic cable. The aligned structure facilitates guided transport of ions along the longitudinal direction. In particular, the ionic cables 1010, 1020 were fabricated by soaking the grass stems into a saturated $LiNO_3$ aqueous solution under vacuum to enhance infiltration. The surface of the ion-soaked grass stem was then covered by a thin thermal shrink tube to prevent the solution from evaporating. The resulting ionic cables 1010, 1020 were attached to ion exchange membranes 1008, 1018 using ion-soaked cotton connectors (not shown) that conduct ions.

The resistance of the ionic cables 1010, 1020 increased almost linearly with the length thereof, indicating a relative constant ionic conductivity. In particular, the conductivity of the ionic cable was calculated to be ~80 mS·cm⁻¹ based on the slope of the resistance-length curve, which is comparable to a pure $LiNO_3$ aqueous solution (~150 mS·cm⁻¹). Moreover, due to the excellent mechanical strength and flexibility, the grass ionic cable 1010, 1020 was capable of being bent into random shapes (similar to a conventional electrical cable) without substantially changing its ionic conductivity. This stable ionic conductivity can be attributed to the structure's long continuous micro-channels, which retain the liquid electrolyte during manipulation and bending.

To characterize the electrochemical performance of the fabricated inverted batteries, multiple discharge voltage profiles were taken at different ionic loads. Unlike a conventional battery setup, the voltage profile of an inverted battery cannot be recorded from its anode 1002 and cathode 1012 directly, since they have already been electrically shorted by the electrical conductor 1026. Instead, a lithium metal reference electrode was placed close to the cathode 1012 to record the voltage profile between them. In particular, electrochemical impedance spectroscopy (EIS) was conducted in a frequency range of 500 mHz to 1 MHz with a 50 mV AC amplitude. To measure the EIS of the grass ionic cables 1010, 1020, two titanium metal strips were attached to the ends of the grass cables where the $LiNO_3$ soaked cotton was used to wrap the metal to the end of the grass cables to achieve ionic connections. The voltage profiles of the inverted battery were then recorded between the cathode 1012 and the lithium metal reference electrode located near the cathode 1012.

Figure 10C:
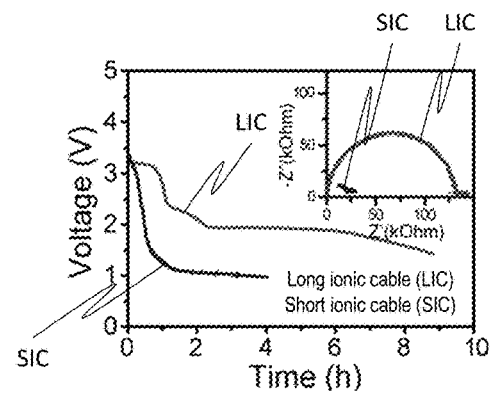
FIG. 10C shows a graph of discharge profiles of a pair inverted battery cells according to the configuration of FIG. 10A that are coupled to ionic cables having different ionic resistances; and, in the inset, a graph of electrochemical impedance spectroscopy (EIS) of the different ionic cables.

The inset of FIG. 10C depicts the resulting EIS spectra of two electron batteries with different ionic cables. Their ionic resistances are calculated to be approximately 30 kΩ for the short ionic cable (SIC) and 135 kΩ for the long ionic cable (LIC). The voltage profiles of these two batteries are shown in the main graph of FIG. 10C, where the inverted battery with the lower resistance (i.e., coupled to SIC) discharges much faster than the one with the higher resistance (i.e., coupled to LIC). Thus, the inverted battery exhibits similar electrochemical behavior to a conventional ion battery. Since the battery with the higher resistance (i.e., coupled to LIC) discharges at a slower rate, the voltage profile displays clear plateaus at ~2 V and ~3 V, which corresponds to $V_2O_5$.

Example 2

To demonstrate interaction with an ionic system, the inverted battery 1000 was used to drive migration of ions in an ionic system. To visualize the process, blue-colored copper ions 1030 were used to demonstrate migration along a $LiNO_3$ solution-soaked cotton string (~1 mm thick, 8 cm long). When the inverted battery 1000 was connected to the cotton string by two grass ionic cables 1010, 1020, lithium ions traveled from the anode 1002 to the cathode 1012 through the external ionic circuit (i.e., cotton string) to generate an ionic current. Initially, the blue-colored ions 1030 were placed at the center of the string. After the inverted battery 1000 was connected to the two ends of the string as shown in FIG. 10C and discharged at a current of ~100 µA for 10 min, the blue colored ions 1030 diffused towards the cathode 1012 side of the battery. The flow of $Li^+$ thus formed an electrical field, which caused the blue-colored copper ions 1030 to drift towards the cathode 1012.

Example 3

Figure 11A:
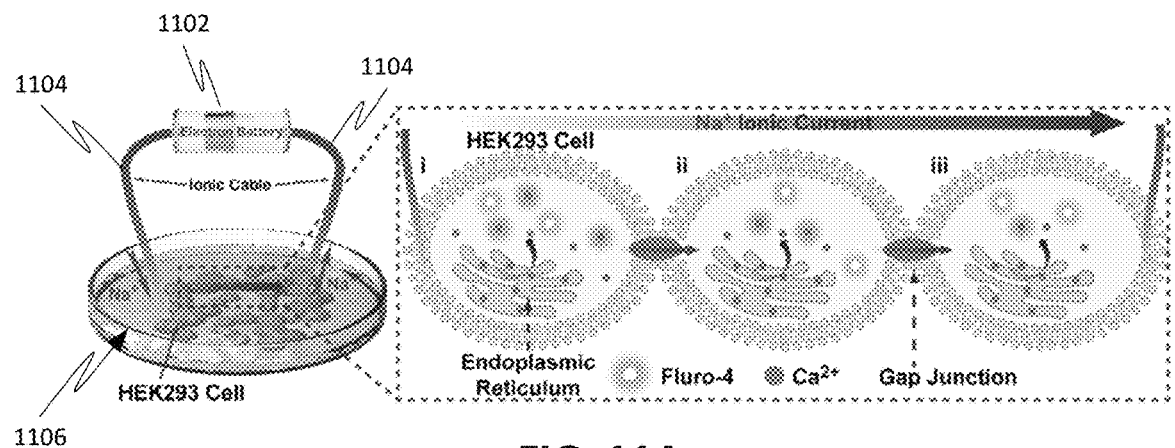
FIG. 11A illustrates an experimental setup for testing generation of ionic current in a biological system using a fabricated example of an inverted battery cell similar to the configuration of FIG. 10A.

As shown in FIG. 11A, cultured living cells (in particular, HEK293 cells) were used to demonstrate the interaction between the inverted battery 1102 and a biosystem 1106. In particular, inverted battery 1102 was used to stimulate movement of calcium ions ($Ca^{2+}$) inside living cells by generating a continuous ionic current. The inverted battery 1102 applied an ionic current to the cells of the biosystem 1106 through ionically conductive cables 1104. In order to make the ions compatible with the living biosystem 1106, the grass ionic cables were soaked with NaCl solution instead of a lithium salt solution. Small electrode tips were constructed using syringe needle tips (similar to the configuration illustrated in FIG. 5B) to enhance contact with the cells. The syringe needle tips had an inner diameter of ~0.5 mm and were filled with 150 mM NaCl in a 1% agarose hydrogel. The electrode materials were sealed in respective lithium organic electrolyte-filled glass tubes by respective ionic exchange membranes. Thus, ion exchange occurred at the interfaces between the electrodes and the grass ionic cables (i.e., at the respective ionic exchange membranes).

Discharge of the inverted battery 1102 results in stimulation of cells in the biosystem 1106, during which the ionic current was about ~30 µA. The ionic current of the drifted $Na^+$ ions from the ionic cables 1104 generates a continuous electric field that stimulates the cells. When the cells were stimulated, $Ca^{2+}$ ions were released from the endoplasmic reticulum (i.e., the intracellular calcium storage pool) through $Ca^{2+}$ channels. Meanwhile, some messengers diffused from the stimulated cell to its neighboring cells through gap junctions and caused internal $Ca^{2+}$ release processes to occur in neighboring cells.

Figure 11B:
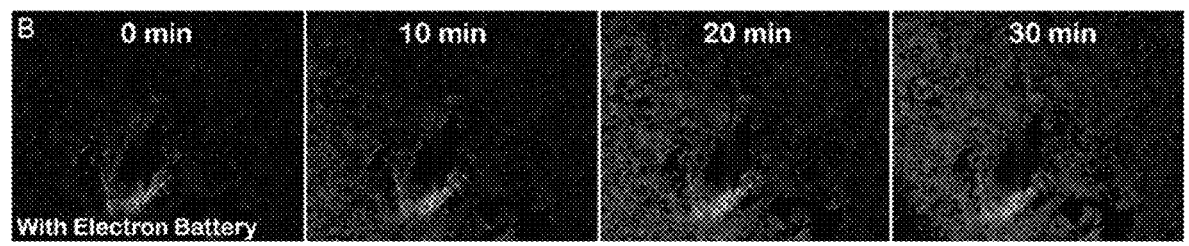
FIGS. 11B-11C are images of the biological system with and without ionic current stimulation by the inverted battery cell, respectively, at different time intervals.
Figure 11C:
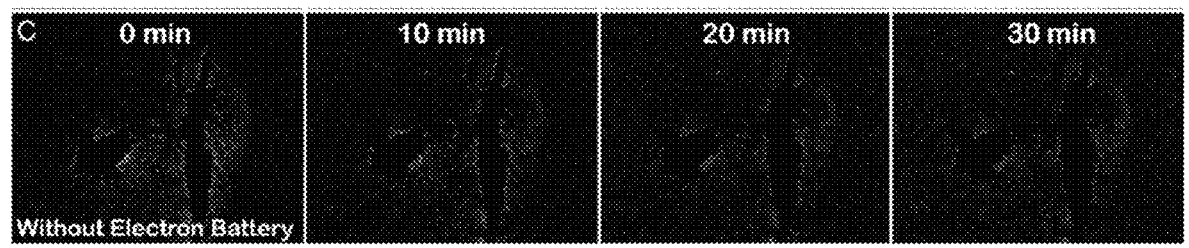

As shown in FIG. 11A, a calcium indicator, Fluro-4, exhibited enhanced green fluorescence upon $Ca^{2+}$ binding and was used to identify the $Ca^{2+}$ concentration in the living cells. FIG. 11B shows the fluorescence intensity changes of the calcium indicator in the living HEK293 cells after stimulation from the inverted battery using ~30 µA of ionic current. The initial fluorescent area at 0 minutes in FIGS. 11B-11C was due to mechanical stimulation from the needle tip at the end of the ionic cable 1104 breaking the monolayer of cultured cells. After the ionic current was applied to the cells, the electrical stimulation caused the release and accumulation of $Ca^{2+}$ ions within the living cells. The binding of $Ca^{2+}$ ions to the fluorescent indicator lead to an increase in the fluorescent intensity. Moreover, due to the interaction between cells, the fluorescence intensity spread along the cells to form a wave-like fluorescent image. After 30 minutes of continuous stimulation from the inverted battery, the fluorescence signal reached nearly all areas surrounding the living cells, as shown in FIG. 11B. A control sample was stimulated by the same needle tips but without any applied ionic current. As shown in FIG. 11C, the cells showed initial fluorescence around the tip-touched areas due to mechanical stimulation, similar to the first panel in FIG. 11B. However, without further stimulation from an inverted-battery-provided ionic current, the mechanical stimulated fluorescence dimmed over time instead of spreading out or getting brighter.

The inverted battery successfully stimulated a $Ca^{2+}$ wave in cultured living cells. Note that $Ca^{2+}$ flows into and out of muscle cells to stimulate muscle movement. Thus, the inverted battery can be used to provide muscle stimulation, among other applications. Moreover, during the stimulation process, the ionic current from the inverted battery did not cause any electrochemical reactions in the biosystem. In contrast, if a conventional battery were used to stimulate the cells, the water within the biosystem would undergo electrolysis in order to generate a continuous ionic current, which would harm the living cells.

Although many of the examples and configurations discussed above relate to the delivery of positive ions from the inverted battery to an ionic system, embodiments of the disclosed subject matter are not limited thereto. Indeed, by appropriate selection of electrode materials and operation of the inverted battery, negative ions could instead be provided by the inverted battery to the ionic system. In such configurations, the negative ions would be generated at the cathode and flow to the anode via the external circuit (e.g., ionic cables and ionic system) during discharge of the inverted battery.

One of ordinary skill in the art will readily appreciate that the above description is not exhaustive, and that aspects of the disclosed subject matter may be implemented other than as specifically disclosed above. Although exemplary chemistries and materials have been discussed above, one of ordinary skill in the art will understand that the teachings of the present disclosure can be extended to other materials and chemistries. Thus, embodiments of the disclosed subject matter are not limited to the specific chemistries and materials discussed herein.

It will be appreciated that some aspects of the disclosed subject matter can be implemented, fully or partially, in hardware, hardware programmed by software, software instruction stored on a computer readable medium (e.g., a non-transitory computer readable medium), or any combination of the above. For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

It is thus apparent that there is provided, in accordance with the present disclosure, inverted battery devices, and systems and methods for use thereof. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A device comprising:
a pair of electrodes, one of the pair being configured as an anode and the other of the pair being configured as a cathode;
a first volume in which a first electrolyte solution and the anode are disposed;
a second volume in which a second electrolyte solution and the cathode are disposed;
first and second ionic conductors; and
an electrical conductor extending between the first and second volumes to couple the pair of electrodes to each other such that electrons travel between the pair of electrodes,
wherein the device is constructed to generate an ionic current in a separate system coupled between the anode and cathode,
each of the first and second volumes has a respective ion exchange membrane, the ion exchange membranes being configured to allow ions to pass therethrough while retaining the first and second electrolyte solutions in the first and second volumes, respectively,
the first ionic conductor has a first end coupled to the ion exchange membrane of the first volume,
the second ionic conductor has a first end coupled to the ion exchange membrane of the second volume, and
each of the first and second ionic conductors has a respective second end constructed for coupling to the separate system.

2. The device of claim 1, wherein each of the second ends of the first and second ionic conductors comprises a second ion exchange membrane that allows ions to pass therethrough while preventing solution from entering or leaving the respective one of the first and second ionic conductors.

3. The device of claim 1, further comprising an ion reservoir coupled between one of the first and second volumes and the separate system, wherein the ionic current in the separate system comprises ions from said ion reservoir.

4. The device of claim 3, wherein the ions in said reservoir comprise drug ions or ionized drug molecules, and the device is constructed to pump the drug ions or the drug molecules to the separate system.

5. The device of claim 1, further comprising an electrical circuit coupled to the electrical conductor such that at least some electrical power used by the electrical circuit is provided by electrons travelling between the pair of electrodes.

6. The device of claim 1, further comprising:
a first switch coupled between one of the pair of electrodes and the separate system, and constructed to open/close an ion conductive path therebetween so as to control flow of the ionic current.

7. The device of claim 1, wherein at least one of the first and second ionic conductors comprises a natural plant with axially-extending lumina.

8. The device of claim 1, wherein:
one of the first and second ionic conductors comprises a cation exchange membrane that allows positive ions to travel therethrough while preventing travel of negative ions therethrough; and
the other of the first and second ionic conductors comprises an anion exchange membrane that allows negative ions to travel therethrough while preventing travel of positive ions therethrough.

9. The device of claim 1, wherein the electrical conductor is electrically connected to the anode via the first electrolyte solution and to the cathode via the second electrolyte solution.

10. The device of claim 1, wherein the anode is formed of lithium, the cathode comprises nanowires formed of vanadium oxide, and the first and second electrolyte solutions comprises a lithium organic electrolyte.

11. The device of claim 1, wherein the electrical conductor provides a short circuit between the pair of electrodes.

12. The device of claim 1, wherein the device is configured as a rechargeable battery.

13. A system comprising:
an ionic system;
first and second ionic conductors; and
an inverted battery coupled to the ionic system and configured to supply ions to generate an ionic current in the ionic system,
wherein the ionic current is generated without a corresponding electron-exchange electrochemical reaction in the ionic system,
the inverted battery comprises:
a pair of electrodes, one of the pair being configured as an anode and the other of the pair being configured as a cathode;
a first volume in which a first electrolyte solution and the anode are disposed;
a second volume in which a second electrolyte solution and the cathode are disposed; and
an electrical conductor extending between the first and second volumes to couple the pair of electrodes to each other such that electrons travel between the pair of electrodes,
each of the first and second volumes has a respective ion exchange membrane configured to allow ions to pass therethrough while retaining the first and second electrolyte solutions in the first and second volumes, respectively,
the first ionic conductor has a first end coupled to the ion exchange membrane of the first volume,
the second ionic conductor has a first end coupled to the ion exchange membrane of the second volume, and
each of the first and second ionic conductors has a respective second end coupled to the ionic system.

14. The system of claim 13, further comprising:
an ion reservoir between the battery and the ionic system,
wherein the supplied ions are from said ion reservoir,
the ions in said reservoir comprise drug ions or ionized drug molecules, and
the inverted battery acts as a pump for delivering the drug ions or the drug molecules to the ionic system.

15. A method comprising:
using ions from an inverted battery to supply ions to an ionic system so as to generate an ionic current in the ionic system without a corresponding electron-exchange electrochemical reaction in the ionic system,
wherein the inverted battery comprises:
a pair of electrodes, one of the pair being configured as an anode and the other of the pair being configured as a cathode;
a first volume in which a first electrolyte solution and the anode are disposed;
a second volume in which a second electrolyte solution and the cathode are disposed; and
an electrical conductor extending between the first and second volumes to couple the pair of electrodes to each other such that electrons travel between the pair of electrodes,
each of the first and second volumes has a respective ion exchange membrane configured to allow ions to pass therethrough while retaining the first and second electrolyte solutions in the first and second volumes, respectively, and
the method further comprises, prior to the using ions from the battery, coupling the inverted battery to the ionic system by a pair of ionic conductors, such that one of the pair of ionic conductors has a first end coupled to the ion exchange membrane of the first volume and a second end coupled to the ionic system, and such that the other of the pair of ionic conductors has a first end coupled to the ion exchange membrane of the second volume and a second end coupled to the ionic system.

16. The method of claim 15, wherein the ionic current has a linear relationship with respect to applied potential and lacks a threshold potential for onset.

17. The method of claim 15, wherein:
the second end of the one of the pair of ionic conductors comprises a cation exchange membrane that allows positive ions to travel therethrough while preventing travel of negative ions therethrough,
the second end of the other of the pair of ionic conductors comprises an anion exchange membrane that allows negative ions to travel therethrough while preventing travel of positive ions therethrough, and
the ionic current causes selective pumping of ions into or out of the ionic system and/or ionic conductors via the cation and anion exchange membranes.

18. The method of claim 15, wherein the supplying ions comprises supplying drug ions or ionized drug molecules to the ionic system.

19. The method of claim 18, wherein the drug ions or ionized drug molecules are from a reservoir between the inverted battery and the ionic system.

20. The method of claim 15, wherein the ionic current stimulates a muscle, nerve, or cellular process in the ionic system.

* * * * *